United States Patent
Abele et al.

(10) Patent No.: US 7,563,410 B2
(45) Date of Patent: Jul. 21, 2009

(54) SOLID PHASE EXTRACTION APPARATUS AND METHOD

(75) Inventors: Karl Abele, Binningen (CH); Robert D. Ricker, Middletown, DE (US)

(73) Assignee: Agilent Technologies, Inc., Santa Clara, CA (US)

( * ) Notice: Subject to any disclaimer, the term of this patent is extended or adjusted under 35 U.S.C. 154(b) by 861 days.

(21) Appl. No.: 10/968,296

(22) Filed: Oct. 19, 2004
(Under 37 CFR 1.47)

(65) Prior Publication Data
US 2006/0083659 A1 Apr. 20, 2006

(51) Int. Cl.
*B01L 11/00* (2006.01)
*B01L 3/00* (2006.01)
*B01D 15/00* (2006.01)
*B01D 37/00* (2006.01)

(52) U.S. Cl. .................. 422/101; 422/99; 422/100; 422/68.1; 210/656; 210/198.2; 210/264; 210/767; 436/178

(58) Field of Classification Search .......... 210/767, 210/656, 321.75, 257, 445, 264, 198.2, 257.2; 422/99–101, 68.1; 436/178
See application file for complete search history.

(56) References Cited

U.S. PATENT DOCUMENTS

| | | | |
|---|---|---|---|
| 4,713,974 A * | 12/1987 | Stone | 73/864.23 |
| 4,902,481 A | 2/1990 | Clark et al. | |
| 4,927,604 A | 5/1990 | Mathus et al. | |
| 5,005,434 A * | 4/1991 | Watanabe et al. | 73/864.21 |
| 5,035,866 A | 7/1991 | Wannlund | |
| 5,047,215 A | 9/1991 | Manns | |
| 5,108,704 A | 4/1992 | Bowers et al. | |
| 5,205,989 A | 4/1993 | Aysta | |
| 5,264,184 A | 11/1993 | Aysta et al. | |
| 5,283,039 A | 2/1994 | Aysta | |
| 5,286,652 A | 2/1994 | James et al. | |
| 5,395,587 A * | 3/1995 | Brigham-Burke et al. | 422/68.1 |
| 5,403,489 A | 4/1995 | Hagen et al. | |
| 5,417,923 A | 5/1995 | Bojanic et al. | |

(Continued)

FOREIGN PATENT DOCUMENTS

EP 0446970 9/1991

(Continued)

OTHER PUBLICATIONS

Hennion, M.C., Solid-phase extraction; method development, sorbents, and coupling with liquid chromatography, Journal of Chromatography A, Elsevier Science B.V., vol. 856, pp. 3-54, Sep. 1999.

*Primary Examiner*—Ana M Fortuna (57) ABSTRACT

Devices, and methods of use thereof, receivable by autosamplers for processing fluids contains suspended solids and solubles in, for example, solid phase extraction, include an inlet chamber in fluid communication with an outlet chamber through an integral fluid pathway. One or more autosampler needle(s) may inject the fluid into the inlet chamber, which contains a separation medium through which the injected fluid flows prior to flowing into the outlet chamber, from which fluid may be withdrawn by the autosampler needle(s). A pressure tight seal may be formed between the needle(s) and inlet chamber, and backflow is preventable from the outlet chamber to the inlet chamber. Numerous embodiments of the device are described, including well plate configurations and structures graspable by autosampler robotic devices and/or which may be held in autosampler trays.

24 Claims, 8 Drawing Sheets

U.S. PATENT DOCUMENTS

| | | | |
|---|---|---|---|
| 5,439,593 A | 8/1995 | Price | |
| 5,567,309 A * | 10/1996 | Classon et al. | 210/233 |
| 5,788,827 A * | 8/1998 | Munson | 204/555 |
| 5,906,796 A | 5/1999 | Blevins et al. | |
| 6,124,012 A | 9/2000 | Jones, Jr. et al. | |
| 6,177,008 B1 | 1/2001 | Treiber et al. | |
| 6,200,533 B1 | 3/2001 | Blevins et al. | |
| 6,491,873 B2 | 12/2002 | Roberts et al. | |
| 6,530,288 B1 | 3/2003 | August et al. | |
| 6,621,076 B1 | 9/2003 | Van de Goor et al. | |
| 6,762,834 B2 * | 7/2004 | Komatani et al. | 356/315 |
| 7,259,019 B2 * | 8/2007 | Pawliszyn et al. | 436/178 |
| 7,288,195 B2 * | 10/2007 | Coville et al. | 210/321.75 |
| 7,468,281 B2 * | 12/2008 | Kallury et al. | 436/178 |
| 2002/0059945 A1 | 5/2002 | Maiefski et al. | |
| 2002/0155033 A1 | 10/2002 | Strand et al. | |

FOREIGN PATENT DOCUMENTS

| | | |
|---|---|---|
| EP | 1329705 | 7/2003 |
| WO | WO00/45164 | 8/2000 |
| WO | WO01/30498 | 5/2001 |
| WO | WO02/097029 | 12/2002 |
| WO | WO03/053534 | 7/2003 |
| WO | WO03/104774 | 12/2003 |
| WO | WO2004/059301 | 7/2004 |

* cited by examiner

SOLID PHASE EXTRACTION APPARATUS AND METHOD

BACKGROUND OF THE INVENTION

Many samples (e.g., of chemical, biological or environmental sample) cannot be injected into chromatographic, nuclear magnetic resonance, or other analytical equipment without prior sample pre-cleaning steps to remove interferences such as particulate matter and soluble contaminants. Injecting such samples without pre-cleaning will lead to temporary or permanent system contamination. Thus labs dealing with such samples often spend 50-70% of their overall analysis time preparing samples for injection into these delicate instruments, including time for enriching and/or concentrating fluid samples.

Current approaches to pre-cleaning are typically offline e.g., U.S. Pat. Nos. 6,200,533 and 6,124,012), and generally involve placing samples in solid phase extraction (SPE) cartridges (typically composed of a polymer such as polyethylene.) SPE cartridges typically comprise tubular or syringe-shaped components filled with a separation medium such as silica gel or derivatized silica gel. Inteferences (components suspended in the sample) are extracted after loading upon the separation medium by washing and eluting. SPE may be tailored to capture or pass specific components in the liquid sample. Analyses of biological samples such as plasma and urine using HPLC generally require SPE to remove both particulate matter and soluble contaminants. SPE can also be used to perform a simple fractionation of a liquid based upon differences in the chemical structure of the component parts.

Existing SPE procedures have a number of disadvantages, including requiring a great deal of manual labor to pipetting the sample and solvents through SPE columns or cartridges. Variations in pipetting volume, speed and time contribute to poor process reproducibility. Reproducibility is a cornerstone to validating manufacturing and/or testing processes, such as, for example, for the purposes of conforming to good manufacturing practices (GMPs) and/or good laboratory practices (GLPs.) Furthermore, the size of conventional SPE devices makes analysis of small volume samples difficult.

Fluid flow through or over the separation medium in the conventional SPE columns and cartridges is driven by gravity or by vacuum (such as described in U.S. Pat. Nos. 4,090,850 and 6,491,873) to an outlet at their respective bottoms. Typically, a separate collection tray or container receives the filtrate passing through the cartridge(s). Samples often flow through the SPE material at different speeds, leading to partial or even complete absorption of the analytes. Thus, some SPE cartridges may run dry during elution, whilst others still have a sufficient amount of solvent.

Multi-well filtration apparatus are also well known in the art, and may be used for the assay of biological liquids. Conventional multi-well filtration plates have 96, 384, or 1536 wells for performing multiple assays simultaneously. Each well is adapted to contain a sample fluid, having a relatively small internal volume defined in part by an interior surface extending downwardly from an opening at an upper surface of the multi-well plate to a bottom outlet and collection tray.

After samples have undergone SPE or filtration processing, they may be injected into the chromatographic instruments manually or by means of autosamplers, automated instruments adapted to receive and/or grasp and manipulate sample containers, such as well plates, trays or vials containing the samples to be injected. Through alignment and movement (typically in multiple dimensions) of one or more injector needles with respect to indexed positions of the sample containers, metered samples are withdrawn and injected into chromatographic instruments. The movement of the needle(s) is guided by a robotic controller executing user programming. Autosamplers that operate on stationary, indexed, multi-well trays, such as Series 1100 HPLC Autosamplers manufactured by Agilent Technologies of Palo Alto, Calif., are in wide use. Alternatively functioning autosamplers are also well known in the art, including those that operate upon racks of individual sample vials, and/or those configured for use with rotatable trays. U.S. Pat. Nos. 6,148,680, 5,286,652, 6,468,475 describe some of these types of autosamplers, all of which may be utilized with the present invention.

One online (real-time) process of solid phase micro extraction has been developed that involves disposing polymer-coated fibers within the injector needle of an autosampler. The fiber is pushed into the sample and allowed to absorb analytes. This method has gained acceptance in water analysis, but to date has been met with limited success in analyzing more viscous matrices. Another online approach utilizes a modified CTC-PAL autosampler integrating independent X-Y-Z movable robotic arms. The capital costs of the analytical instrument and the additional robotic manipulator are frequently so high as to negate any productivity gained by the automation.

It would, therefore, be desirable to automate the SPE instrumentation and method in a relatively inexpensive manner. A system that accurately, robustly and reproducibly moves the SPE process into an online, standard analytical workflow, leveraging conventional autosampling equipment, would be of great benefit. A further benefit would accrue to any instrument that enables analysis of biological samples by HPLC (LC/MS) methods.

SUMMARY OF THE INVENTION

In one aspect, the present invention provides an integrated structure such as a well plate for use with liquid chromatographic (LC) and mass spectrophotometric (MS) autosampling equipment such as, for example, Series 1100 Autosamplers manufactured by Agilent Technologies of Palo Alto, Calif., that access wells and/or reservoirs from the top side of the well plate. A SPE plate in accordance with the present invention generally includes a unitary structure having an inlet chamber in fluid communication with an outlet chamber through an integral fluid pathway, a separation medium disposed in the inlet chamber such that a fluid injected by the one or more autosampler needle(s) into the inlet chamber are transported to the outlet chamber after traversing the separation medium. The well plate structure may form a pressure tight seal between the inlet chamber and the autosampler needle(s), and prevent gravitational flow of fluids between the inlet chamber and outlet chamber. In one aspect, the well plate is capable of integrating, for example, in an indexed array or network, numerous sample positions, SPE inlet and outlet chambers, and solvent and waste reservoirs such that a plurality of SPE functions may be performed automatically by injections and extractions of relevant fluids by the autosampler needle.

In another aspect, the present invention provides structures such as, for example, SPE devices that may be manipulated by autosamplers that incorporate or are used in conjunction with transport and alignment robotics. Usage with these types of autosamplers involves gripping the SPE device with robotic grasping devices and transporting the SPE device into alignment with the needle(s) of the autosampler.

A structure such as, for example, an SPE device, in accordance with the present invention may also be used with autosamplers that employ multiple needles for simultaneously injecting and/or withdrawing fluids from distinct chambers and/or reservoirs on the SPE device.

In another aspect, the present invention provides a system for automating an SPE process, including an inventive SPE device of a type described above in conjunction with any of a variety of conventional autosamplers.

The present invention also provides automated SPE and/or other fluid processing methods that employ injections and extractions of fluids (e.g., samples, solvents and waste) to and from the inventive structure to condition the separation material, load the sample onto/through the separation material, and sequentially elute matrix and analyte fractions from the separation material, after which they may be reconstituted in a more aqueous solvent composition also utilizing the autosampler functions.

Thus, pre-cleaning of samples, including complex chemical and biological samples, can be advantageously integrated into a standard analytical workflow with reproducible sample preparation conditions (i.e., precisely controlled flow rates, solvent volumes, and timing between sample preparation and chromatographic analysis.) In one aspect, fluid flow through the SPE device is driven by the metering piston of the autosampler, rather than by using a vacuum or gravity-driven approach and, thus, is independent of backpressure variations in the SPE device. The precise timing also eliminates the possibility that the separation material of the SPE device will dry out and lead to irreversible absorption of analytes on the separation material. Proper packing of the separation material can also contribute to improved reproducibility.

BRIEF DESCRIPTION OF THE FIGURES

The various features and aspects of the present invention may be more readily understood with reference to the following detailed description taken in conjunction with the accompanying drawings, where like reference numerals designate like structural elements, and in which.

DETAILED DESCRIPTION OF THE INVENTION

Figure 1:
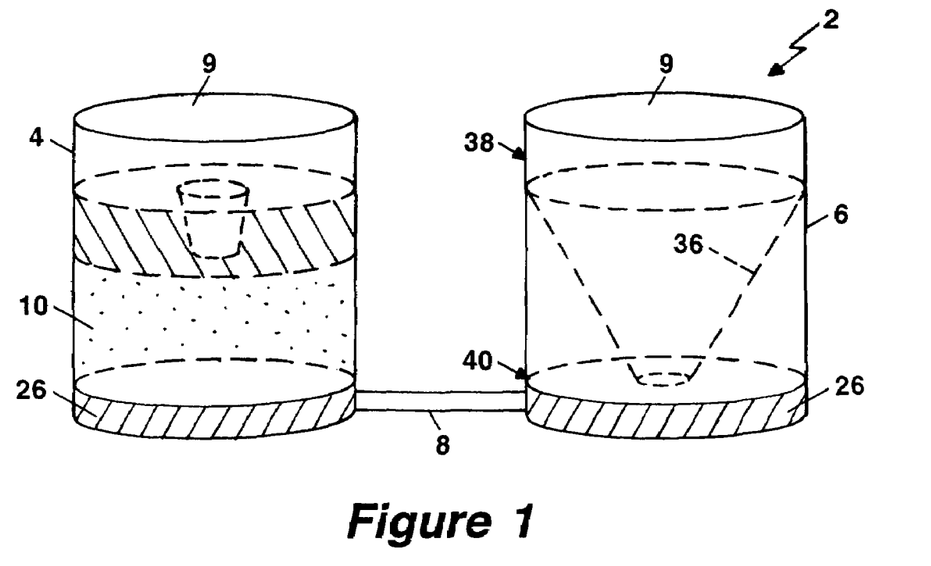
FIG. 1 is a side view of a SPE device structure in accordance with one aspect of the present invention.

FIG. 1 illustrates a SPE device 2 for use in automated SPE processing of a volume of aqueous fluid containing suspended solids and/or solubles. The device 2 is shaped and dimensioned to be received by an autosampler (not shown.) One well plate configuration of the device 2 is described below for use with chromatographic and spectrophotometric autosamplers (and related well plate feeders), while another configuration of device 2 is adapted for use with autosamplers including robotic grasping devices (e.g., fingers) that typically operate by grasping and transporting sample chambers (e.g., sample vials) into a position aligned with the autosampler's needle.

Figure 4:
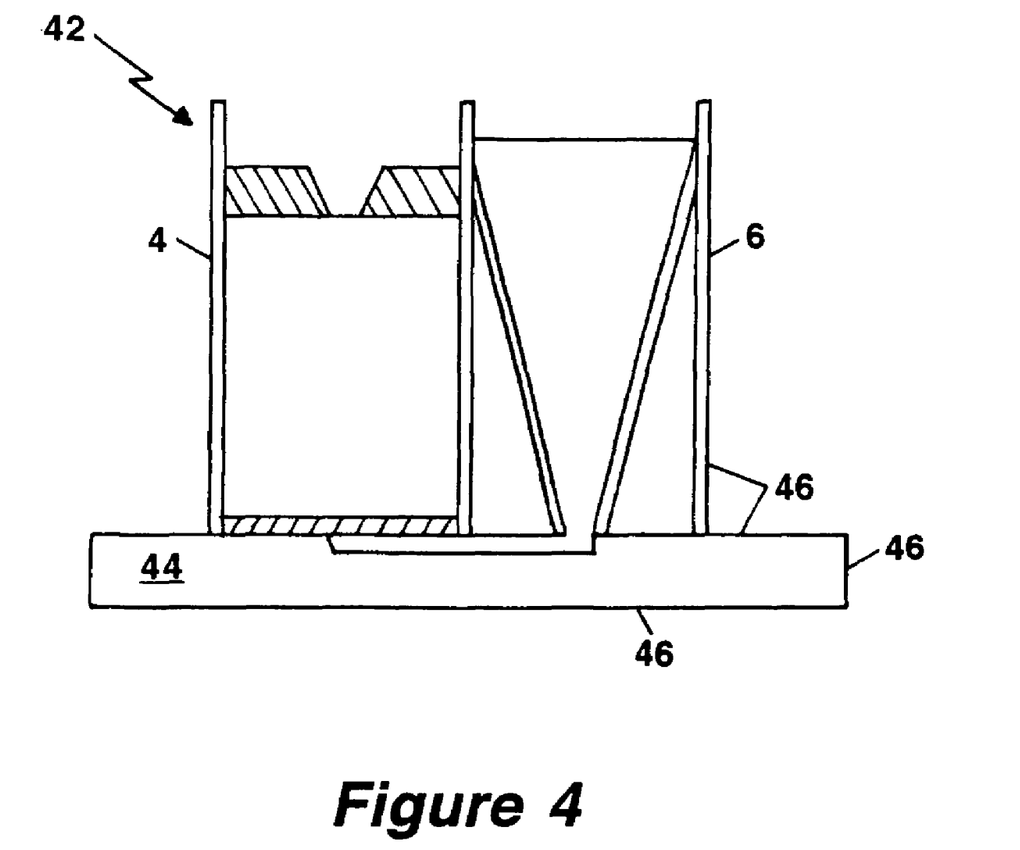
FIGS. 4A-4B are illustrations of SPE device structures in accordance with one aspect of the present invention, adapted for use with autosampler gripping robotics.
Figure 4A:
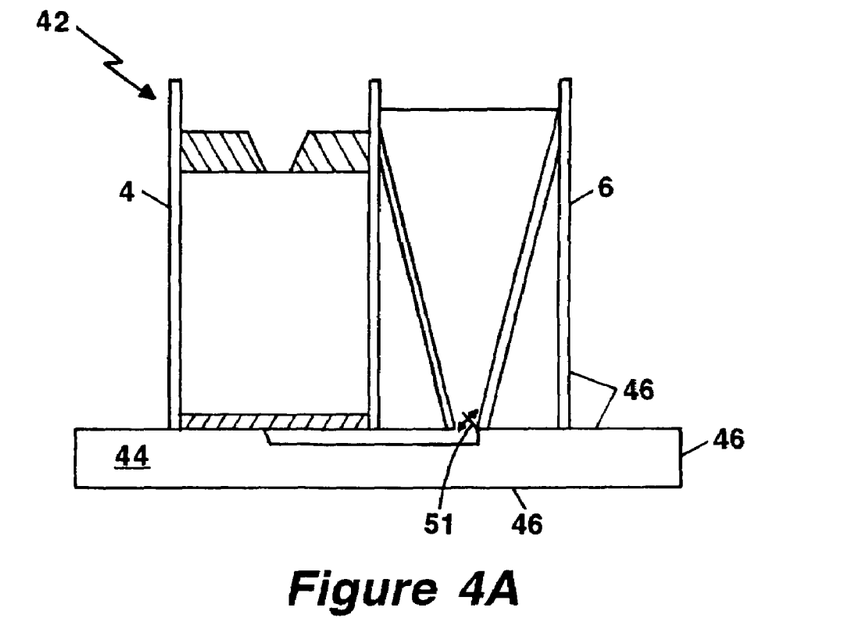
Figure 4B:
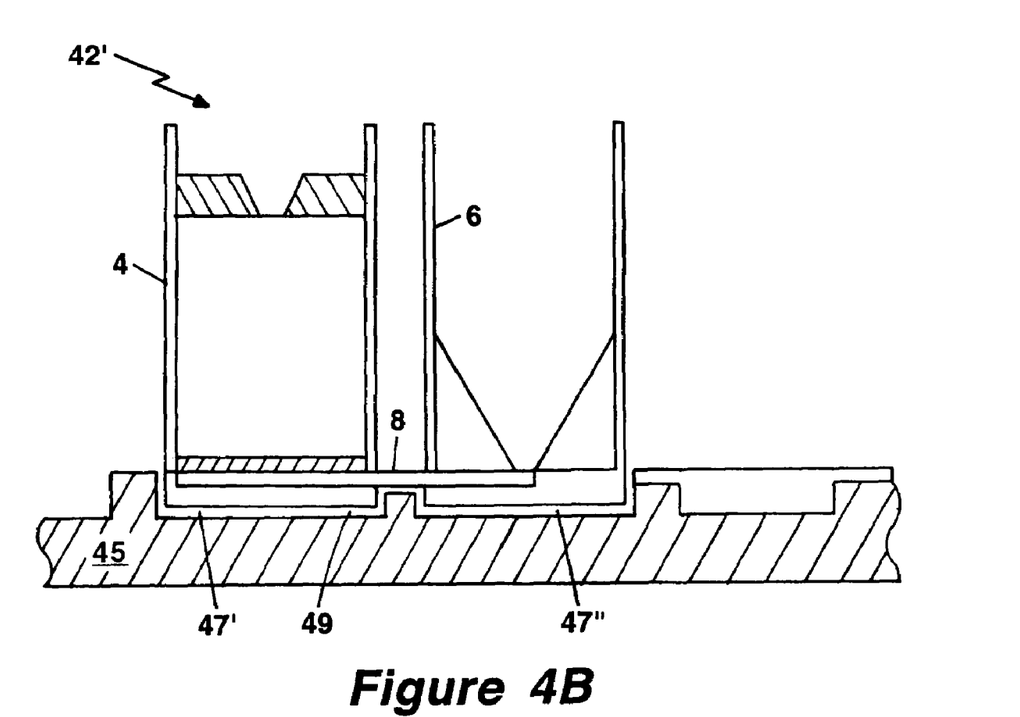

Device 2 generally includes an inlet channel or chamber 4 in fluid communication with an outlet channel or chamber 6 through a fluid pathway 8. The inlet chamber 4, outlet chamber 6, and fluid pathway 8 are integrated in a unitary structure that may be formed as a unitary element or as multiple components securely (and preferably unalterably) connected together. At the top of the inlet chamber 4 and outlet chamber 6 are opening 9 through which an autosampler needle may access their respective volumes. A separation medium 10 contained in the inlet chamber 4 serves to separate any solid phase present in a sample injected into inlet chamber 4 as the sample traverses the separation medium 10 prior to being transported through the fluid pathway 8 to the outlet chamber 6. As used herein, the phrase "separation medium" means any material that causes suspended solids and/or solubles to separate from the solution in which they are suspended. This includes chromatographic sorbents such as porous silica derivatized with with octadecyl ($C_{18}$) or octyl ($C_8$) functional groups, or porous particles based on organic polymer. The separation material may alternatively be composed of affinity-based medium for biological sample processing, or reactive and/or ion exchange media. Fluid pathway 8 may comprise one or more polymeric conduits of any cross-sectional geometry (e.g., circular or rectangular) connecting respective openings at or near the bottoms of inlet chamber 4 and outlet chamber 6. Note that the fluid pathway is shown connecting to the bottoms of the respective chambers, other designs are possible such as, for example, wherein the fluid pathway connects to the side of the respective chambers (such as shown in FIG. 4B.) The injected fluid, however, should traverse the separation medium 10 prior to transport by the fluid pathway to the outlet chamber.

Figure 2A:
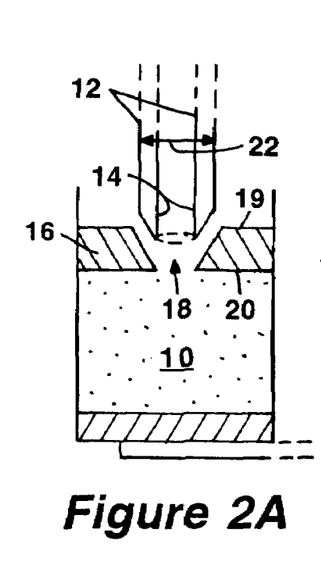
FIGS. 2A-2C are illustrations of an inlet chamber of the SPE device in accordance with one aspect of the present invention.
Figure 2B:
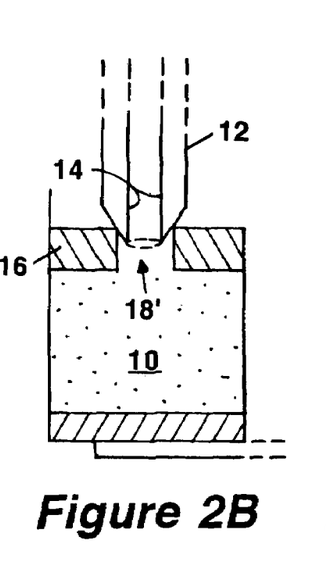
Figure 2C:
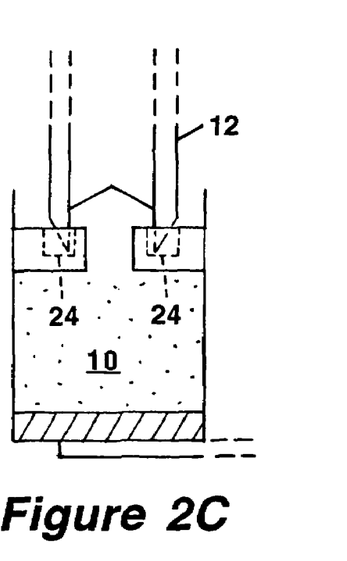

With reference to FIGS. 2A-2C, device 2 further includes a sealing element for forming a pressure tight seal with an autosampler needle 12 in order to form an enclosed path for injected fluids to follow. As used herein the phrase "pressure tight" means leak free up to about 10 bar (150 psi.) A metering pump of the autosampler provides tight control over the volume and flow rates of fluids injected through needle 12. Typical autosampler injections are on the order of 0.2 to 100 µL, but may be lower or higher (e.g., up to about 3 mL.) In one aspect, a needle is provided having a sufficiently wide inner diameter to transport and inject sufficient volumes of conditioners, solvents and potentially viscous, complex chemical and biological (e.g., whole blood, urine, plasma, tissue, etc.) matrices involved in SPE processing. The SPE device 2 may additionally be used with autosamplers that simultaneously access (i.e., injecting into and/or withdrawing from) more than one position (e.g., sample position and/or reservoir) at a time.

The pressure tight seal between the needle 12 may be formed between a cap 16 and the typically tapered tip 14 of the needle 12. Cap 16 is preferably disposed in the inlet chamber 4 at a position above the separation material 10, and may be a press fit component placed in inlet chamber 4 before or after separation material filling, or alternatively may be an integrally formed feature of inlet chamber 4. Cap 16 includes a central bore 18 through which injected fluids will pass during injection from the needle 12. As shown in FIG. 2A, the bore 18 of cap 16 may be tapered to mate with the taper of needle tip 14, preferably in a conical shape having an inner diameter greater than the diameter 22 of the needle at the top 19 of the bore but smaller than the needle diameter at the bottom 20 of the bore. Alternative designs of the cap 16 may also serve as the means for forming the pressure tight seal, such the cap 16 shown in FIG. 2B that has a circular bore 18', or the cap 16 shown in FIG. 2C that has a circular groove 24 in which the needle tip 14 may be seated. If the needle(s) employed do not possess tapered tips, alternative geometries adapted to mate with non-tapered needles may alternatively be utilized.

Referring again to FIG. 1, device 2 may also include a blocking element preventing gravitational flow of fluids between the inlet chamber 4 and outlet chamber 6 potentially corrupting the SPE process. FIG. 4A shows a flap mechanism 51 disposed at the base of outlet chamber 6 that allows fluids to flow into outlet chamber 6 but blocks gravitational flow back out of chamber 6. Flap mechanism 51 could also be disposed at some other position between the inlet chamber and outlet chamber. Gravitational flow may also be prevented by one or more frits 26 disposed in either or both of the inlet chamber 4 and outlet chamber 6 at either end of the fluid pathway 8. The frits 26 may exhibit hydrophobic properties and/or block fluid flows not driven by sufficient fluid pressure. The inlet chamber 4, outlet chamber 6, and fluid pathway 8 may also be dimensioned so capillary adhesion action may provide the anti-gravitational forces necessary to prevent gravitational flows. Hydrophobic properties may be inherent in the materials selected for forming the device, or may result from chemical treatment (e.g. with silicone or Teflon™.)

Figure 3A:
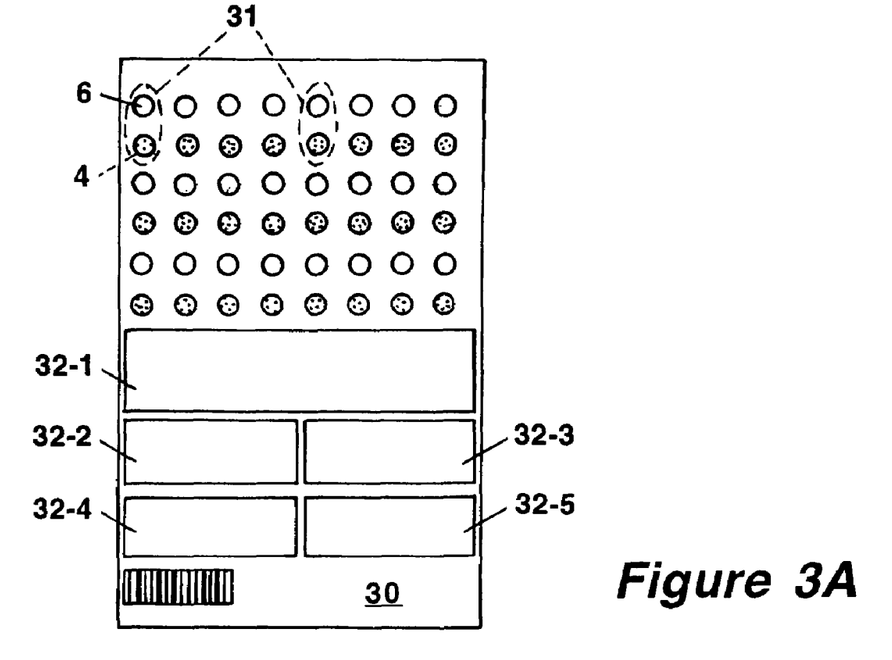
FIG. 3A is a top view of a well plate embodiment of an SPE device in accordance with one aspect of the present invention.

A top view of an SPE well plate 30 in accordance with the present invention is illustrated in FIG. 3A. The well plate 30 may be formed of standard polymeric materials, such as polyethylene or polypropylene. Plate 30 is shown configured to process 24 samples, however plate design choices could lead to a greater or fewer number of pairs 31 of inlet chambers 4 and outlet chambers 6. Plate 30 is additionally configured with a number of reservoirs 32, including reservoirs for waste 32-1, conditioner 32-2, wash/rinse fluid 32-3, solvent 32-4, and/or any other fluid 32-5 desired, such as, for example, for reaction processing steps. Obviously, a single plate 30 could be configured with none, some or all of these reservoirs 32 as desired or required by the particular SPE process being performed. Well plates such as plate 30 are easily adopted into a standard, analytical workflow including analytical equipment with only minor modifications, thereby increase reproducibility of sample preparation, as all samples can be processed under precisely reproducible conditions (i.e., flow rates, defined solvent volumes, timing between sample preparation and chromatographic analysis, etc.) Obviously, draw volumes and draw rates should be matched to the sample to be processed and/or chamber sizes being utilized. Although sample positions are not integrated in this version of the plate 30, samples can be drawn from a second plate in the autosampler.

In an example by no means meant to limit the scope of the invention:
- the conditioning 32-2, wash 32-3 and elute 32-4 reservoirs each may have 16 ml volumes;
- up to 0.6 ml per inlet chamber 4 from each reservoir can be used (solvent consumption with 0.6 ml/channel=14.4 ml);
- the separation material comprises 100-200 mg of stationary phase ($C_{18}$, $C_8$, SiOH, etc.);
- the waste reservoir may hold a volume of the three other reservoirs (~50 ml); and
- the autosampler needle wash can be accomplished in a conventional autosampler wash port.

Figure 3B:
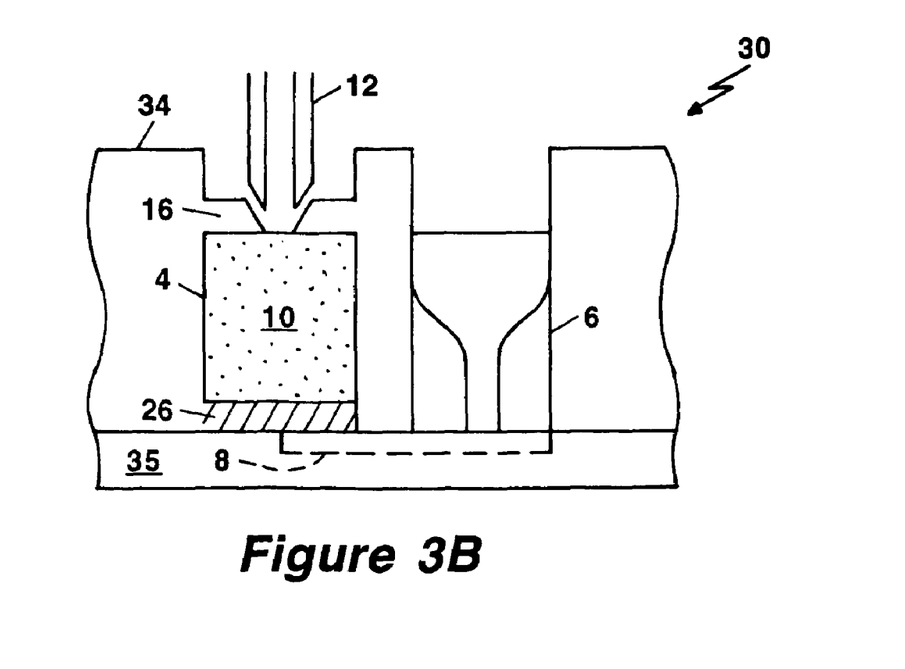
FIG. 3B is a partial side cross-sectional view of a well plate embodiment of an SPE device in accordance with one aspect of the present invention.

FIG. 3B presents a partial cross-sectional view of plate 30, encompassing the integrated inlet chamber 4/outlet chamber 6 structure linked by fluid pathway 8. The chambers extend downward from a surface 34 of the plate 30, and the fluid pathway 8 may comprise a transfer channel printed in a polypropylene base 35 of the plate 30. Both the frit 26 and cap 16 may also be composed of polypropylene. Through controlled injections into inlet chamber 4 and extractions from outlet chamber 6 by autosampler needle 12, an automated SPE process comprised of sequential absorption/desorption of analytes and matrix compounds on the separation medium 10 can be performed. Injection volumes often are selected to be roughly three times (3×) the volume of separation medium utilized.

Figure 3C:
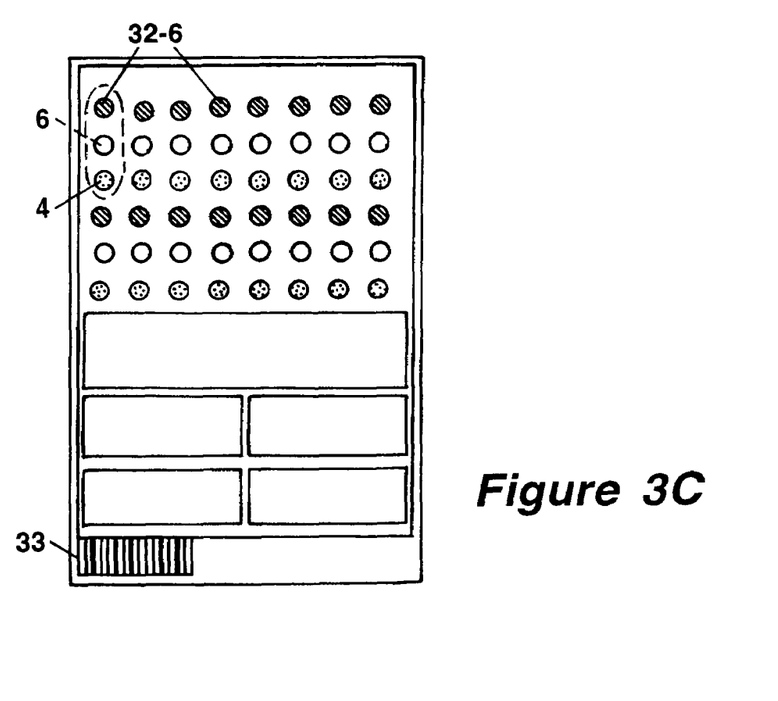
FIG. 3C is a top view of an alternative well plate embodiment of an SPE device in accordance with one aspect of the present invention.

FIG. 3C illustrates an alternative version of well plate 30. This variant integrates indexed sample wells 32-6 on the plate that may be filled manually prior to initiating the SPE process, or may be filled automatically by the autosampler, as many autosamplers have the capability to dispense fluids from cartridges or containers (not shown) separate from the well plates upon which they operate. Another feature of note is bar code 33, which serves as a unique identifier of well plate 30. As the automated SPE process may be inserted into a standard analytical workflow, reading the bar code 33 with a bar code reader (not shown) would assist an operator in creating an electronic record of the processing conditions (e.g., the number of channels, etc.) utilized during the SPE processing. Certain autosamplers have the ability to uniquely identify well plates by detecting the relative positions of mechanical tabs present on the surface of well plates. The unique identifier could also comprise some other form of identification (e.g., radiofrequency tag or magnetic label.) The identifier facilitates compliance with governmental record-keeping requirements, such as Good Laboratory Practices (GLP's) and electronic recordkeeping requirements (e.g., "Part 11" FDA regulations.)

With reference again to FIG. 1, note that the outlet chamber 6 is partially defined by an inner surface 36 having a taper or conical shape arranged such that fluids (e.g., eluted fractions) can be more efficiently withdrawn. Alternative non-linear geometries that work on a similar principle(s) of picking up eluting fractions (and other fluids) with needles shaped to approximate the outline of the inner surfaces of outlet chamber 6 (such as the design of microvials for autosamplers like Agilent PN 5183-4731, PN 9301-0978 and PN 9301-0977), or of constraining a larger volume of the fluid near the top 38 of outlet chamber 6 than the bottom 40 may also be utilized, and even chambers having no taper may be uses (however less efficiently.) Additionally, inlet chamber 4 is shown as having no taper to its inner surface, but could easily be formed with non-uniform cross-sectional dimensions just as outlet chamber 6 has been formed. For example, some conventional SPE cartridges are known that have syringe-like or frustoconical shapes, some of which could eliminate the need in inlet chamber 4 to be equipped with frit 26.

Figure 3D:
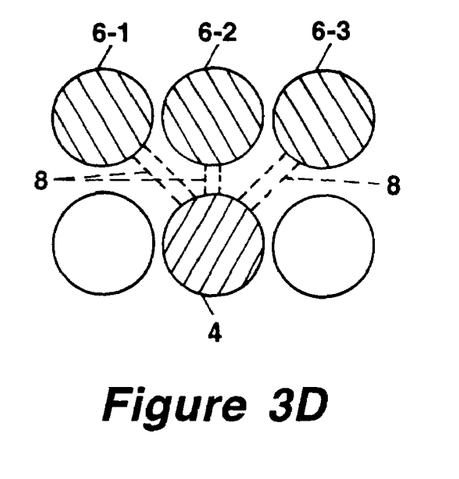
FIGS. 3D-3F are illustrations showing alternative configurations of inlet and outlet chambers of SPE devices in accordance with one aspect of the present invention.
Figure 3E:
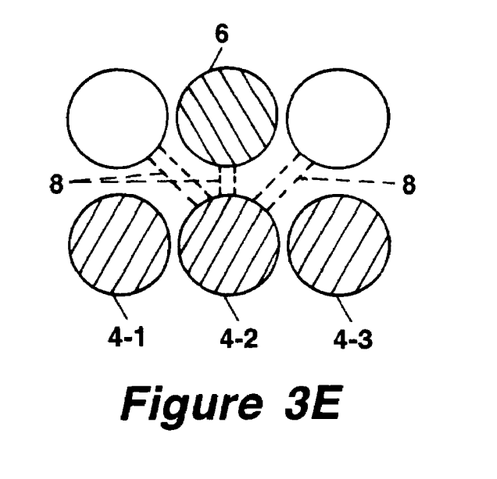
Figure 3F:
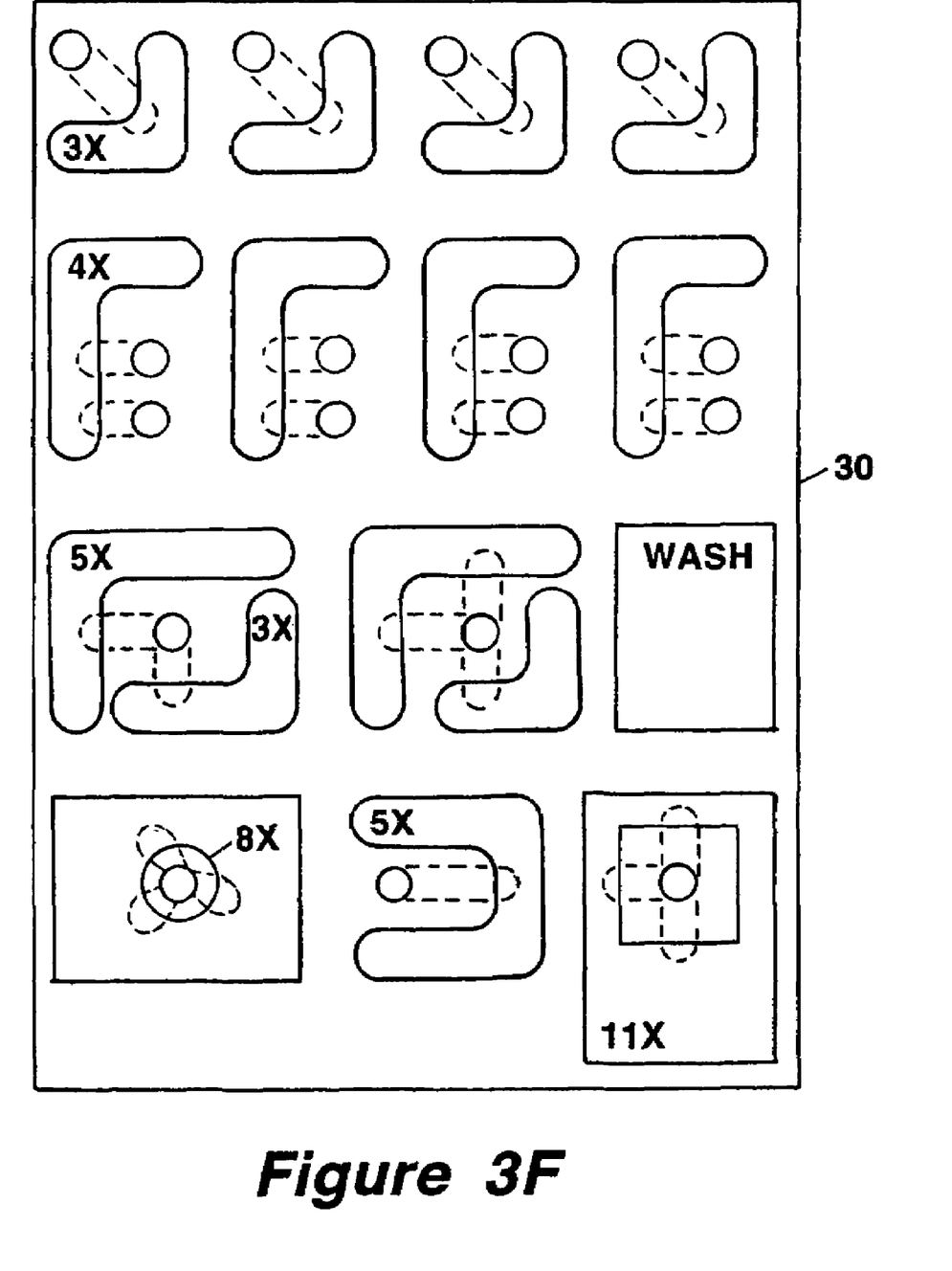

Although the well plates illustrated in the figures are rectangular, as noted above the present invention is by no means limited to such geometries. For example, rotary autosamplers are configured to receive circular trays, and could easily be adapted to receive circular well plates, provided that each position on the SPE device 2 is individually addressable by the needle controller of the autosampler. In addition, FIGS. 3D-3F illustrate that the one-to-one relationship described thus far between the inlet chamber 4 and outlet chamber 6 is not a requirement of the present invention. Although at least one inlet chamber 4 and one outlet chamber 6 must be integrated, there may be a need for multiple outlet chambers 6-1, 6-2, 6-3 (FIG. 3D) and/or multiple inlet chambers 4-1, 4-2, 4-3 (FIG. 3E.) The layout of well plate 30 illustrated in FIG. 3F is intended to demonstrate that there exists a high number of possible chamber and/or reservoir arrangements, and that the geometries and volumes of the chambers and/or reservoirs are not limited, except by the ability of the autosampler needle(s) to access the chambers or reservoirs. There may even be configurations, such as the "8×" and "11×", wherein the outlet chambers are concentrically disposed around the inlet chamber with which it is in fluid communication (i.e., wherein exemplary fluid pathways are indicated by the dotted lines.)

FIG. 4A illustrates a structure 42 configured for use with an autosampler of a type well known in the art that operates by gripping and transporting a fluid container (e.g., a sample vial) into precise alignment with the autosampler needle(s) through use of robotics (arms and fingers). Structure 42 is simply a variant of SPE device 2 that, rather than being embedded in a well plate, may comprise a free-standing module or, alternatively, connected to additional inlet chamber 4/outlet chamber 6 pairs to accommodate the requirements of the particular autosampler utilized. The inlet chamber 4 and outlet chamber 6 (frit-less in this example) are integrally formed with the fluid pathway 8, and protrude upward from a substrate or base 44. Any of a number of exterior surfaces 46 of structure 42 may be grasped by the robotic fingers or arms of the auto sampler.

FIG. 4B illustrates yet another embodiment of a structure in accordance with one aspect of the present invention. Structure 42' is configured such that inlet chamber 4 and outlet chamber 6 may be mateably secured into wells 47',47" of an autosampler tray 45. Lower portions of the inlet chamber 4 and outlet chamber 6 are dimensioned to allow stable seating into wells 47',47" in order that the tray may be manipulated without spillage. The fluid pathway 8 is illustrated as bridging the wells over a well divider 49, however well divider 49 could have a groove (not shown) to accommodate fluid pathway 8.

A description of an automated SPE workflow according to one aspect of the invention will now be presented with reference to FIGS. 5A-5E, referring again to the well plate 30 described above, and additionally utilizing a commercially-available sample plate 48 consisting of an indexed network of sample wells accessible by the autosampler needle(s). Note that samples could be dispensed automatically from a sample container other than sample plate 48, provided the autosampler has such a capability. Each of the operations that follow are performed automatically by the autosampler controller that controls the movements and fluid flows in the autosampler needle. Solvent and sample transfer between the different positions on plate 30 is ideally performed by an autosampler system suited for larger volume injections (e.g., the 1100 Series Autosampler with 900 µl upgrade from Agilent Technologies.) Clearly, a vast number of alternative steps could be envisioned by those of skill in the art depending on the sample size and required amounts of separation material and solvent needed, including, but not limited to: (a) repetitions of particular steps; (b) cleaning of the needle (or needles) used; and/or (c) extraction of waste from outlet chamber 6 to waste reservoir 32-1 after (or contemporaneously in multi-needle autosamplers) each injection.

Figure 5A:
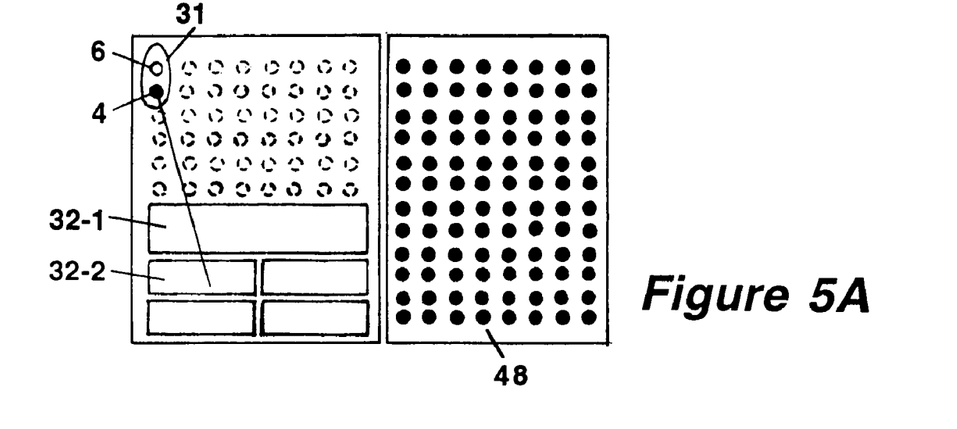
FIGS. 5A-5E are illustrations of a well plate embodiment of the present invention demonstrating an exemplary SPE process workflow.

In an optional but preferable conditioning step shown in FIG. 5A, a solvent (e.g., water or an organic solvent such as methanol or acetonitrile), usually but not necessarily containing buffers (salts) for pH definition, is withdrawn/extracted from the conditioner reservoir 32-2 and injected by the autosampler needle (not shown) into the inlet chamber 4 to "wet" the SPE separation material and rinse any contaminants from inlet chamber 4 and prepare the separation material to preferentially retain the target components by defining the loading properties of polar functions (e.g., silanol groups) of the separation material. It is advantageous for the SPE device 2 to have a high capacity for retaining target compounds of a wide range of chromatographic polarities and to be capable of maintaining target compound retention as sample interferences are washed to waste.

Figure 5B:
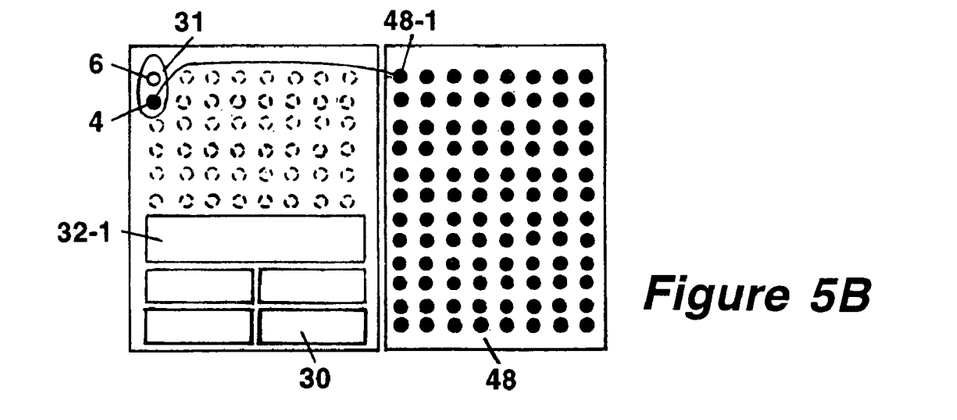

In a loading step shown in FIG. 5B, a sample (including analytes and matrix) will be loaded onto the separation material, through pickup at sample position 48-1 and injection into inlet chamber 4. During the loading step, either sample molecules or matrix molecules or sample molecules and matrix molecules will be absorbed by the separation material in inlet chamber 4.

Figure 5C:
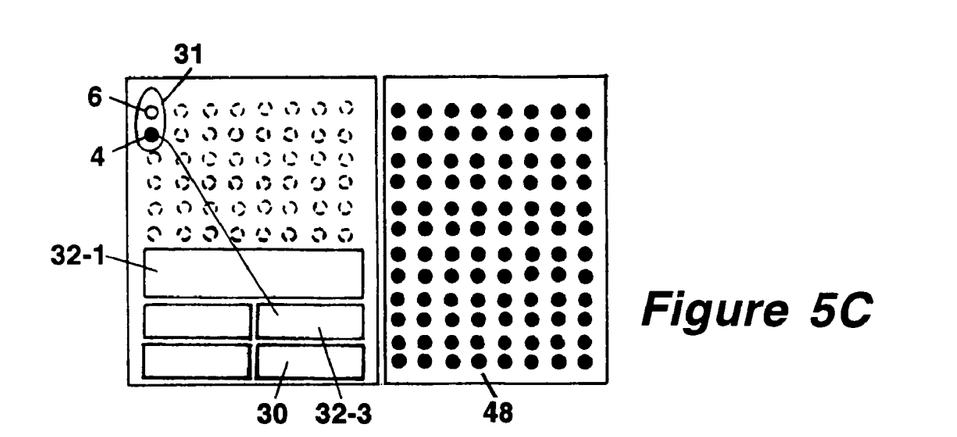
Figure 5D:
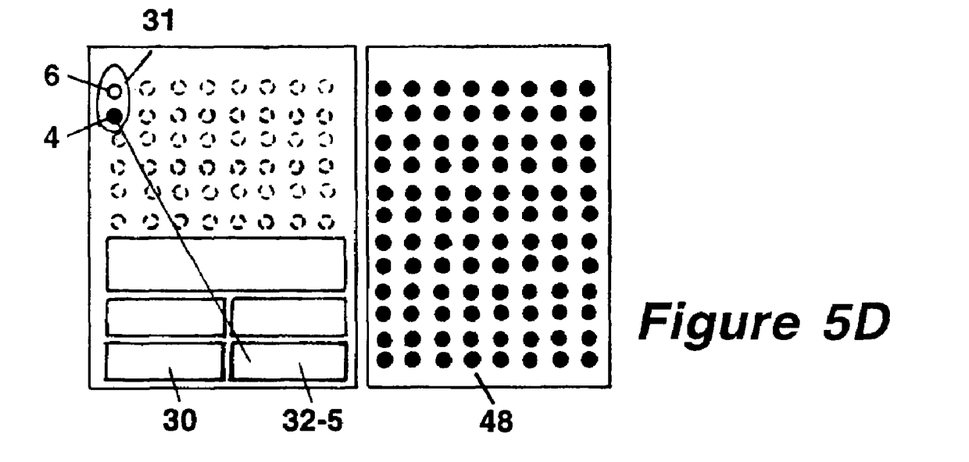
Figure 5E:
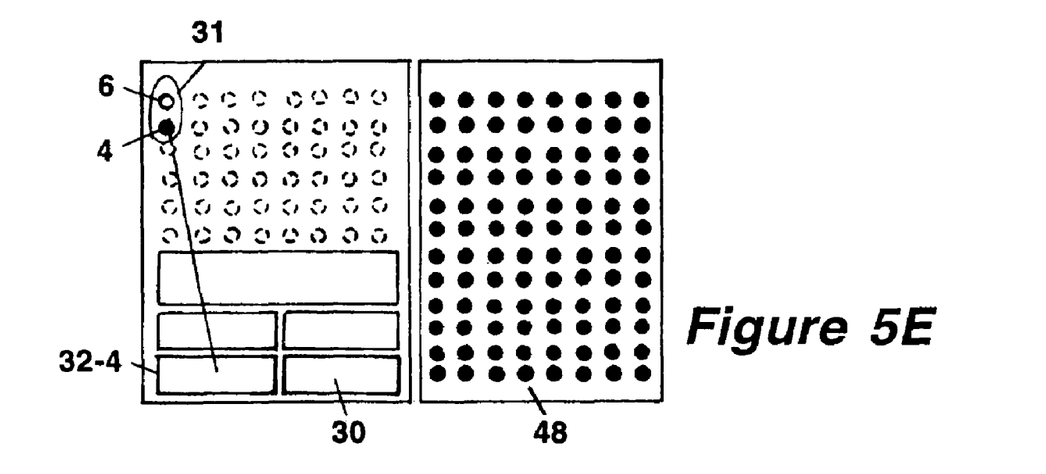

In subsequent steps shown in FIGS. 5C-5E usually referred to as "washing" or "elution" steps, the matrix and the analyte molecules absorbed by the separation material will be sequentially eluted therefrom and retrieved from outlet chamber 6 for possible immediate injection onto, for example, an HPLC column, or for reconstitution. During these steps, the robotic SPE system (including the well plate 30 and autosampler) will deliver wash (from reservoirs 32-3 and/or 32-5) and elute (from elute reservoir 32-4) solutions to the inlet chamber 4, and retrieve waste and eluting fractions from outlet chamber 6. The elute fraction containing the analytes can be reconstituted in a more aqueous solvent composition using the standard autosampler functions, i.e., by drawing additional water from a defined position and mixing with the fraction containing the analyte. In many cases, a higher aqueous content of solvent will improve HPLC performance with large volume injections. Sample focusing can be done either on the analytical column or on an integrated pre-column system (using known column-switching techniques.)

Although the invention has been described with respect to various SPE embodiments, it should be realized this invention is also capable of a wide variety of further and other embodiments within the spirit and scope of the appended claims.

We claim:

1. A device for use in processing a volume of fluid that contains suspended solids and solubles, comprising: a structure receivable by an autosampler and integrating a first inlet chamber in fluid communication with a first outlet chamber through an integral fluid pathway, each chamber accessible at a top opening by one or more autosampler needle(s); and a separation medium disposed in the first inlet chamber such that a fluid injected by the one or more autosampler needle(s) into the first inlet chamber traverse the separation medium prior to transport through the pathway to the first outlet chamber, wherein gravitational flow of fluids between the first inlet chamber and first outlet chamber is prevented by at least one blocking element.

2. The device of claim 1, further comprising a sealing element to form a pressure tight seal between the first inlet chamber and the one or more autosampler needle(s).

3. The device of claim 1, further comprising a bored cap disposed at the top of the first inlet chamber and shaped to partially receive one of the one or more needle(s) so as to form a pressure tight seal between the first inlet chamber and the one or more autosampler needle(s).

4. The device of claim 1, wherein the at least one blocking element preventing the gravitational flow is positioned between the first inlet chamber and the first outlet chamber.

5. The device of claim 1, wherein the first outlet chamber has a larger interior cross-section at the top opening than at an opening to the fluid pathway.

6. The device of claim 1, wherein the structure further comprises one or more volumes accessible at a top opening by the one or more autosampler needle(s) selected from the group consisting of sample positions, waste reservoirs, wash reservoirs, fractionation reservoirs, fraction-pooling reservoirs, reaction reservoirs, and solvent reservoirs.

7. The device of claim 1, wherein the structure comprises a well plate and the first inlet chamber and first outlet chamber comprise portions of an indexed array of wells extending downward from an upper surface of the well plate.

8. The device of claim 1, wherein the structure includes a base and the first inlet chamber and first outlet chamber protrude upwardly from the base, the first inlet chamber being in spaced relation to the first outlet chamber.

9. The device of claim 1, wherein the first inlet chamber is partially defined by a frustoconically shaped inner surface having a wider interior cross section at the top opening than at a second end proximate the fluid pathway.

10. The device of claim 1, wherein the fluid pathway comprises at least one conduit between the first inlet chamber and first outlet chamber.

11. The device of claim 1, further comprising at least one feature selected from the group consisting of at least a second inlet chamber in fluid communication with the first outlet chamber, and at least a second outlet chamber in fluid communication with the first inlet chamber.

12. The device for claim 1, further comprising a unique identifier for the structure disposed on a surface of the structure.

13. A system for processing a volume of aqueous fluid that contains suspended solids and solubles, comprising: an autosampler including one or more needle(s) through which a fluid can he drawn in and ejected out by action of a metering device and further including means for aligning the needle at an injection position or a withdrawal position; a structure integrating a first inlet chamber in fluid communication with a first outlet chamber through an integral fluid pathway, each chamber accessible at a top opening by the one or more needle(s); and a separation medium disposed in the first inlet chamber such that a fluid injected by the one or more needle(s) into the first inlet chamber are transported to the outlet chamber through the fluid pathway after traversing the separation medium, wherein gravitational flow of fluids between the first inlet chamber and first outlet chamber is prevented by at least one blocking element.

14. The system of claim 13, further comprising a sealing element to form a pressure tight seal between the first inlet chamber and the one or more autosampler needle(s).

15. The system of claim 13, wherein the blocking element is positioned between the first inlet chamber and the first outlet chamber.

16. The system of claim 13, wherein the alignment means comprises a robotic arm upon which the needle is movable in three dimensions to indexed positions on the structure.

17. The system of claim 13, wherein the alignment means further comprises a robotic arm having gripper fingers for gripping and moving the structure from an indexed position on a tray to a position proximate the needle, and further robotic means for moving the needle to a fluid injection or extraction position at the inlet chamber or outlet chambers, respectively.

18. A device for use in processing a volume of fluid that contains suspended solids and solubles, comprising: a structure receivable by an autosampler and integrating a first inlet chamber in fluid communication with a first outlet chamber through an integral fluid pathway, each chamber accessible at a top opening by one or more autosampler needle(s); and a separation medium disposed in the first inlet chamber such that a fluid injected by the one or more autosampler needle(s) into the first inlet chamber traverse the separation medium prior to transport through the pathway to the first outlet chamber, wherein the structure includes a base and the first inlet chamber and first outlet chamber protrude upwardly from the base, the first inlet chamber being in spaced relation to the first outlet chamber.

19. The device of claim 18, further comprising a sealing element to form a pressure tight seal between the first inlet chamber and the one or more autosampler needle(s).

20. The device of claim 18, further comprising a bored cap disposed at the top of the first inlet chamber and shaped to partially receive one of the one or more needle(s) so as to form a pressure tight seal between the first inlet chamber and the one or more autosampler needle(s).

21. The device of claim 18, wherein gravitational flow of fluids between the first inlet chamber and first outlet chamber is prevented by at least one blocking element.

22. The device of 18, wherein the at least one blocking element preventing the gravitational flow is positioned between the first inlet chamber and the first outlet chamber.

23. The device of claim 18, wherein the first outlet chamber has a larger interior cross-section at the top opening than at an opening to the fluid pathway.

24. The device of claim 18, wherein the structure further comprises one or more volumes accessible at a top opening by the one or more autosampler needle(s) selected from the group consisting of sample positions, waste reservoirs, wash reservoirs, fractionation reservoirs, fraction-pooling reservoirs, reaction reservoirs, and solvent reservoirs.

* * * * *

UNITED STATES PATENT AND TRADEMARK OFFICE
CERTIFICATE OF CORRECTION

| | | |
|---|---|---|
| PATENT NO. | : 7,563,410 B2 | Page 1 of 1 |
| APPLICATION NO. | : 10/968296 | |
| DATED | : July 21, 2009 | |
| INVENTOR(S) | : Karl Abele et al. | |

It is certified that error appears in the above-identified patent and that said Letters Patent is hereby corrected as shown below:

In column 9, line 33, in Claim 12, delete "for" and insert -- of --, therefor.

In column 9, line 39, in Claim 13, delete "he" and insert -- be --, therefor.

In column 9, line 40, in Claim 22, delete "of" and insert -- of claim --, therefor.

Signed and Sealed this

Fifteenth Day of September, 2009

David J. Kappos
*Director of the United States Patent and Trademark Office*